United States Patent
Inoue et al.

(10) Patent No.: US 7,162,004 B2
(45) Date of Patent: Jan. 9, 2007

(54) MEDICAL IMAGING DIAGNOSIS APPARATUS

(75) Inventors: Yoshihiro Inoue, Kyoto (JP); Kohshiro Sugimura, Joyo (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/075,116

(22) Filed: Mar. 8, 2005

(65) Prior Publication Data

US 2005/0207530 A1 Sep. 22, 2005

(30) Foreign Application Priority Data

Mar. 18, 2004 (JP) .............................. 2004-077578

(51) Int. Cl.
*A61B 6/03* (2006.01)
*G01T 1/166* (2006.01)

(52) U.S. Cl. ...................... 378/4; 378/63; 250/363.04

(58) Field of Classification Search .................... 378/4, 378/63; 250/363.04, 363.05
See application file for complete search history.

(56) References Cited

U.S. PATENT DOCUMENTS 5,682,414 A * 10/1997 Saito .......................... 378/146
6,754,520 B1 * 6/2004 DeSilets et al. ............. 600/415
6,810,103 B1 * 10/2004 Tybinkowski et al. ......... 378/20
6,831,961 B1 * 12/2004 Tybinkowski et al. .......... 378/4
6,961,606 B1 * 11/2005 DeSilets et al. ............. 600/415
2004/0262525 A1 * 12/2004 Yunker et al. .......... 250/363.08

FOREIGN PATENT DOCUMENTS

JP 7-20245 1/1995
JP 11-164829 6/1999

\* cited by examiner

*Primary Examiner*—Edward J. Glick
*Assistant Examiner*—Chih-Cheng Glen Kao
(74) *Attorney, Agent, or Firm*—Rankin, Hill, Porter & Clark LLP

(57) ABSTRACT

A PET gantry and a CT gantry are placed in parallel such that the CT gantry becomes remoter to a common examination couch having a movable couch table top board mounted with a subject person and the CT gantry is made to be movable. The gantries are controlled by a control portion in a console. At first, the CT gantry is moved in a left direction to separate from the PET gantry so that whole body CT scan is carried out for the subject person in a direction from the leg portion to the head portion. Successively, the subject person is passed through a tunnel portion from the leg portion to the head portion by moving the couch table top board in a right direction in a state of considerably separating the CT gantry from the PET gantry to thereby carry out whole body PET scan.

3 Claims, 2 Drawing Sheets

MEDICAL IMAGING DIAGNOSIS APPARATUS

This application claims foreign priority based on Japanese patent application JP 2004-077578, filed on Mar. 18, 2004, the contents of which is incorporated herein by reference in its entirety.

BACKGROUND OF THE INVENTION

1. Field of the Invention

The present invention relates to a medical imaging diagnosis apparatus preferable for early detection of the cancer or the like, particularly relates to a medical imaging diagnosis apparatus capable of taking both of a PET (positron emission tomography) image and an X-ray CT image.

2. Description of the Related Art

PET examination obtains a distributed image (tomographic image) of a positron emitting nuclide at a specific section of a subject person by calculation. After labeling a drug having a property of gathering to the focus of the cancer by a positron emitting nuclide, the drug is administered into the human body. In positron annihilation, gamma rays are emitted in directions opposed to each other by 180° and therefore, the gamma rays are detected at 360° surrounding of the human body to catch simultaneous incidence of the two gamma rays. Since the nuclide is disposed on a line connecting positions of the incidence, data of the line connecting the positions of incidence is provided as position data. The distributed image of the nuclide is reconstructed by collecting the position data for a constant period of time to subject to operational processing. The distributed image (tomographic image) represents a size and a shape of the cancer focus per se and therefore, direct diagnosis can be carried out. However, since the PET image only represent a state of accumulating and distributing the nuclide, it is not necessarily clear at what location of the human tissue the nuclide is present.

Meanwhile, according to an X-ray CT apparatus, by rotating an X-ray tube and an X-ray detector at a surrounding of the body axis of the subject person, X-ray projection data (absorption distribution data) from respective directions in a section orthogonal to the body axis are collected. Then, by subjecting the projection data to back projection, an image (X-ray CT image) of an X-ray absorption rate distribution at the section is reconstructed. The X-ray CT image represents the shape of the tissue at inside of the human body at the section.

Hence, in order to carry out ensured diagnosis, it is effective to use both of the PET image and the X-ray CT image. In a related art, there has been conceived a medical imaging diagnosis apparatus placing a PET apparatus and an X-ray CT apparatus in parallel relative to a single common examination couch, or integrally constituting the PET apparatus and the X-ray CT apparatus to be able to take a PET image and a CT image for the same subject person.

However, even in the case of placing the PET apparatus and the X-ray CT apparatus in parallel or even in the case of integrally constituting the PET apparatus and the X-ray CT apparatus, the subject person is inserted into tunnel portions of cabinets referred to as gantries of the both apparatus. Therefore, blocked feeling or oppressed feeling of the subject person poses a problem.

Further, JP-A-7-20245 describes a system of using a PET apparatus and an X-ray CT apparatus and an examination couch common thereto. However, according to the system, data provided by the X-ray CT apparatus is intended to use for correction of absorption of PET data and the system does not intend to provide a CT image for diagnosis from the X-ray CT apparatus. Further, nothing is conceived for improving blocked feeling or oppressed feeling which the subject person undergoes when the subject person passes tunnel portions of both of the PET apparatus and the X-ray CT apparatus.

Further, JP-A-11-164829 shows an X-ray CT apparatus for carrying out helical scan while continuously moving a gantry of the X-ray CT apparatus relative to a subject person fixed onto an examination couch, and there is not a description with regard to blocked feeling or oppressed feeling which the subject person undergoes.

SUMMARY OF THE INVENTION

It is an object of the invention to provide a medical imaging diagnosis apparatus capable of taking both of a PET image and an X-ray CT image of the same subject person and improved to alleviate blocked feeling or oppressed feeling which a subject person undergoes in examination.

In order to achieve the above-described object, a medical imaging diagnosis apparatus according to the invention comprising:

an examination couch having a couch table top board for a subject person capable of moving the subject person in a body axis direction;

a PET gantry for collecting a PET data arranged to be proximate to the examination couch;

a CT gantry for collecting an X-ray CT data placed in parallel with the PET gantry at a position remoter to the examination couch than the PET gantry;

a moving apparatus for moving the CT gantry in the body axis direction of the subject person relative to the examination couch; and a control portion for controlling the moving apparatus and the examination couch and controlling to collect the CT data while moving the CT gantry and controlling to collect the PET data while moving the couch table top board of the examination couch relative to the PET gantry.

The CT data is collected while moving the CT gantry for collecting the Ct data. Therefore, at this occasion, the CT gantry is separated from the PET gantry for collecting the PET data, an interval therebetween is gradually increased and therefore, blocked feeling or oppressed feeling undergone by the subject person who is being inserted into the tunnel portion of the CT gantry data is alleviated. Further, after finishing to collect the CT data in this way, when the PET data is collected, in a state in which the CT gantry is considerably separated from the PET gantry and the interval therebetween is increased, the couch table top board is moved relative to the PET gantry, the subject person is inserted into the tunnel portion of the PET gantry, and the PET data is collected. Therefore, blocked feeling or oppressed feeling undergone by the subject person can be alleviated.

DETAILED DESCRIPTION OF THE INVENTION

Next, a medical imaging diagnosis apparatus embodying the invention will be explained in reference to the drawings.

Figure 1:
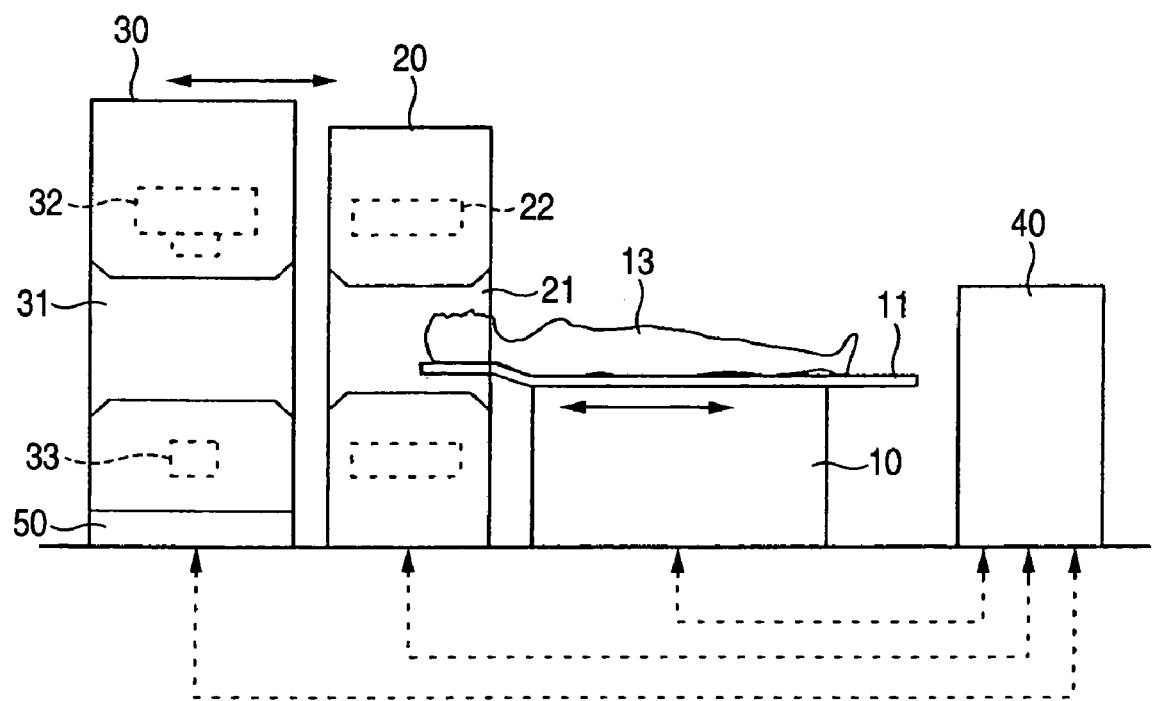
FIG. 1 is a schematic view showing an embodiment of the invention.

As shown by FIG. 1, a medical imaging diagnosis apparatus according to the invention includes an examination couch 10, a PET gantry 20, a CT gantry 30, and a console 40. The PET gantry 20 is a gantry for collecting PET data and is formed with a tunnel portion 21 at a center portion thereof and radiation detectors 22 for collecting the PET data. The radiation detectors 22 are arranged in a ring-like shape to surround the tunnel portion 21.

The tunnel portion 21 of the PET gantry 20 is for inserting a subject person 13 administered with a radioactive drug thereinto. A radiation emitted from the radioactive drug in the body of the subject person 13 is detected by the radiation detectors 22 arranged in the ring-like shape at a surrounding of the tunnel portion 21. Two of the radiation detectors 12 arranged in the ring-like shape detect simultaneous incidence of gamma rays emitted in directions opposed to each other by 180° when a positron emitting nuclide is annihilated. Then, position data of presence of the radioactive drug on a straight line connecting the two radiation detectors 22 is collected.

The CT gantry 30 is a gantry for collecting X-ray CT data and is formed with a tunnel portion 31 at a center thereof and is provided with a rotating mechanism (not illustrated in the drawing) for rotating an X-ray tube 32 and an X-ray detector 33 at a surrounding of the tunnel portion 31. The X-ray detector 33 is a one-dimensional detector having a predetermined length and by rotating the X-ray detector 33 and the X-ray tube 32, a section of the subject person 13 inserted into the tunnel portion 31 is scanned by an X-ray to thereby collect X-ray absorption distribution data from respective directions.

The examination couch 10 is used commonly for the PET gantry 20 and the CT gantry 30. There is established a positional relationship in which the PET gantry 20 and the CT gantry 30 are placed in parallel in this order from a side proximate to the examination couch 10 and the subject person 13 mounted on a couch table top board 11 is inserted into the tunnel portions 21 and 31. That is, the tunnel portions 21 and 31 are arranged to align centering on the body axis of the subject person 13. Further, the couch table top board 11 is moved in a left and right direction of the drawing, that is, in the body axis direction of the subject person 13 as shown by an arrow mark above the examination couch 10.

Further, also the CT gantry 30 is moved in the body axis direction of the subject person 13. The CT gantry 30 is provided with a moving apparatus 50. For example, the moving apparatus 50 comprises a moving frame having a wheel and a motor and the CT gantry 30 is mounted thereabove. Further, the moving apparatus 50 is moved in the left and right direction of the drawing, that is, the body axis direction of the subject person 13 as shown by an arrow mark on a rail (not illustrated) or the like extended in a direction of the examination couch 10 (in the body axis direction of the subject person 13).

The console 40 is provided with a control portion for controlling the examination couch 10, the PET gantry 20, the CT gantry 30 and the moving apparatus 50 and is installed with an input apparatus of a keyboard, a mouse or the like and an image monitor apparatus. Further, in this case, a PET image reconstructing portion and a CT image reconstructing portion are contained in the console 40. That is, the control portion in the console 40 reconstructs a PET image and a CT image by controlling to collect PET data and collect CT data and processing collected data and controls to move the couch table top board 11 of the examination couch 10 and move the CT gantry 30.

Next, operation of the medical imaging diagnosis apparatus constituted in this way will be explained. In this case, PET examination and CT examination are carried out for the whole body of the subject person 13. The subject person 13 is previously administered with a drug labeled by a positron emitting nuclide of FDG or the like. When a state of accumulating the drug to the cancer focus is reached after elapse of 40 minutes through 60 minutes, the subject person 13 is laid on the couch table top board 11 of the examination couch 10.

At this occasion, when an instruction of starting to examine is inputted by operating a keyboard or the like of the console 40, the control portion in the console 40 issues an instruction of starting to collect CT data to the CT gantry 30 and issues an instruction of starting to move the moving apparatus 50. Then, the CT gantry 30 starts to move to a left side from a state of FIG. 2(a) (The state of FIG. 2(a) is a state in which the CT gantry 30 is mostly proximate to the PET gantry 20, the couch table top board 11 is moved in a direction of the CT gantry 30 and the leg portion of the subject person 13 is inserted into the tunnel portion 31 of the CT gantry 30).

That is, the CT gantry 30 is moved from the leg portion to the head portion of the subject person 13 and the subject person 13 is inserted into the tunnel portion 31 successively from the leg portion to the upper half of the body. When the CT gantry 30 passes the head portion of the subject person 13 as shown by FIG. 2(b), the whole body has been scanned by the X-ray from the leg portion to the head portion. Thereby, CT data in the respective sections from the leg portion to the head portion of the subject person 13 have been collected (it is also possible to arrange the subject person 13 on the couch table top board 11 such that the leg portion and the head portion of the subject person 13 are reversed, that is, the leg portion is disposed on a left side of the drawing and the head portion is disposed on a right side thereof). The CT data may be collected by carrying out helical scan by continuously moving the CT gantry 30 while continuously rotating the X-ray tube 32 and the X-ray detector 33. Alternatively, the CT gantry 30 may be moved in steps, and when the CT gantry 30 is stopped to move, the X-ray tube 32 and the X-ray detector 33 may be rotated at each time of stopping to move the CT gantry 30 so that the CT data may be collected at each stop position.

In this way, in collecting the CT data, the CT gantry 30 is separated from the PET gantry 20, an interval between the CT gantry 30 and the PET gantry 20 is widened. The subject person 13 is inserted only into the tunnel portion 31 of the CT gantry 30, and when the subject person 13 passes the tunnel portion 31, the subject person 13 comes out to an open space widened between the CT gantry 30 and the PET gantry 20. Therefore, blocked feeling or oppressed feeling by passing the tunnel portion 31 is alleviated to a considerable degree.

Figure 2:
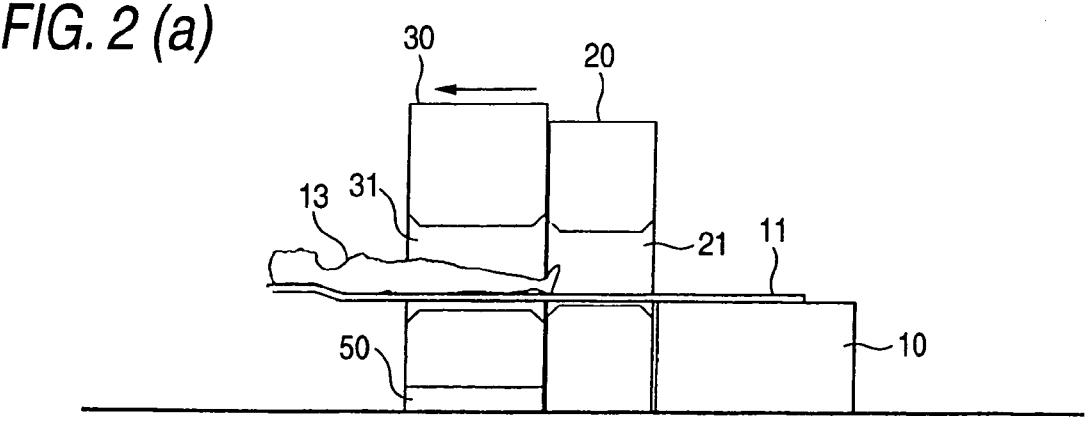
FIGS. 2(a) to (c) illustrate schematic views showing respective states for explaining operation of the embodiment.
Figure 2:
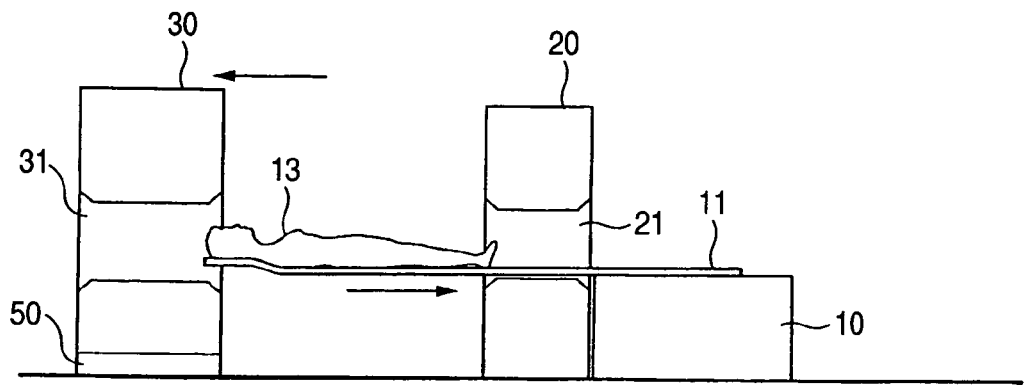
Figure 2:
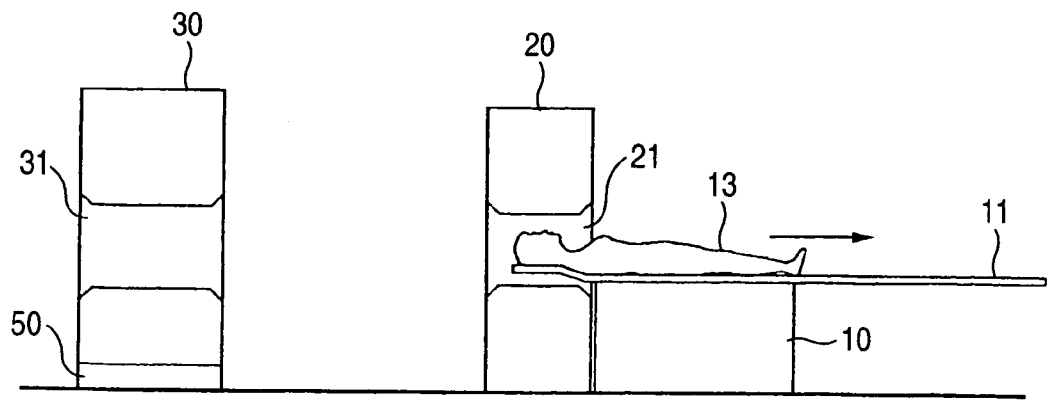

Next, successively, the examination couch 10 is controlled by the control portion, the couch table top board 11 is moved in a right direction as shown by an arrow mark of FIG. 2(b) and PET scan is carried out for the whole body of the subject person 13. At this occasion, the couch table top board 11 is moved in a direction of the leg portion of the subject person 13 relative to the fixed PET gantry 20 and the subject person 13 is successively inserted into the tunnel portion 21 of the PET gantry 20 from the leg portion to the head portion. In this way, as shown by FIG. 2(c), when PET scan up to the head portion has been finished, PET data of the whole portion of the subject person 13 from the leg portion to the head portion has been collected.

In collecting the PET data, as shown by FIGS. 2(b), (c), the CT gantry 30 is considerably separated from the PET gantry 20 and front and rear sides of the PET gantry 20 constitute open spaces. Therefore, although the subject person 13 inserted into the tunnel portion 21 of the PET gantry 20 undergoes blocked feeling or oppressed feeling only when the subject person 13 is brought into the tunnel portion 21, the subject person 13 does not undergo blocked feeling or oppressed feeling before being brought into the tunnel portion 21 and when coming out from the tunnel portion 21. Thus, blocked feeling or oppressed feeling is alleviated as a whole.

When the CT data and the PET data are collected with regard to the whole body of the subject person 13 in this way, the CT image and the PET image are reconstructed from the respective data, the images are displayed at the image monitor apparatus of the console 40 to be subjected to diagnosis of a doctor. The doctor can carry out precise diagnosis of the cancer or the like by comparing and investigating the two images. In this case, the CT data can also be used for absorption correction of the PET data. Further, not only the CT image and the PET image can be formed to display independently from each other but also a fusion image can be formed to display by synthesizing the images.

Further, according to the above-described, after finishing to move the CT gantry 30 for CT scan of the whole body, the couch table top board 11 is started to move for PET scan of the whole body. However, the couch table top board 11 may be moved simultaneously while moving the CT gantry 30 and CT scan of the whole body and PET scan of the whole body may be carried out simultaneously in moving the CT gantry 30 and the couch table top board 11.

Further, although the PET image reconstructing portion and the CT image reconstructing portion are contained in the console 40, the PET image reconstructing portion and the CT image reconstructing portion can be constituted separately from each other and in that case, there is constituted a system of coupling a PET apparatus and a CT apparatus constituted individually by the control portion.

In the case of using both of the PET image and CT image for diagnosis, the malignant tumor of the cancer or the like can be detected by a probability higher than that in the case of using single ones of the images. However, in order to take the PET image and the CT image, it is necessary to pass the subject person through the tunnel portions of the respective gantries, and at that occasion, blocked feeling or oppressed feeling which the subject person undergoes poses a problem. According to the invention, the medical imaging diagnosis apparatus alleviating the above-described problem can be realized by a comparatively simple and inexpensive constitution of arranging the CT gantry to a side remoter to the examination couch than the PET gantry and making the CT gantry movable and moving the couch table top board of the examination couch relative to the fixed PET gantry.

What is claimed is:

1. A medical imaging diagnosis method performed in a medical imaging diagnosis apparatus having an examination couch having a couch table top board for a subject person, a PET gantry for collecting PET data, and a CT gantry for collecting X-ray CT data, the method comprising:
   moving the couch table top board in a direction of the CT gantry from a state in which the CT gantry is placed in parallel with the PET gantry and at a position most proximate to the PET gantry so that the subject person is inserted into the CT gantry at one end portion of the CT gantry,
   moving the CT gantry in a direction away from the PET gantry so that the subject person is inserted into the CT gantry from the one end portion to the other end portion of the CT gantry for a CT scan of the whole body of the subject person while collecting the X-ray CT data by the CT gantry; and
   moving the couch table top board in a direction of the PET gantry so that the subject person is inserted into the PET gantry from one end portion to the other end portion of the PET gantry for a PET scan of the whole body while collecting the PET data by the PET gantry during a single examination.

2. The medical imaging diagnosis method according to claim 1, wherein after finishing moving of the CT gantry for the CT scan of the whole body, the couch table top board starts to move for the PET scan of the whole body.

3. The medical imaging diagnosis method according to claim 1, wherein the step of moving the couch table top board is performed simultaneously with the step of moving the CT gantry so that the CT scan of the whole body and the PET scan of the whole body is carried out simultaneously while moving the CT gantry and the couch table top board.

* * * * *